United States Patent [19]
Newman

[11] Patent Number: 5,215,719
[45] Date of Patent: Jun. 1, 1993

[54] INCENSE BURNER
[75] Inventor: Mark R. Newman, Tucson, Ariz.
[73] Assignee: Jeffrey J. Richards, Phoenix, Ariz.; a part interest
[21] Appl. No.: 684,598
[22] Filed: Apr. 12, 1991
[51] Int. Cl.$^5$ ............................................. A62B 11/00
[52] U.S. Cl. .................. 422/126; 131/240.1; 131/190
[58] Field of Search ........... 422/126, 165, 305; 131/176, 190, 191, 198.1, 238, 240.1; D27/162, 164, 167, 168, 193, 194; D11/131.1; 267/166, 167, 174, 178, 28, 108

[56] References Cited
U.S. PATENT DOCUMENTS

| | | | |
|---|---|---|---|
| 2,182,916 | 11/1937 | Orsinee | 131/240.1 |
| 2,210,291 | 5/1938 | Herr | 131/240.1 |
| 2,630,316 | 3/1953 | Foster | 267/166 |
| 3,426,762 | 3/1967 | Vitale | 131/240.1 |
| 3,958,917 | 5/1976 | Naz | 422/126 |
| 4,155,979 | 5/1979 | Powell | 422/126 |
| 4,281,672 | 8/1981 | Caraway | 131/240.1 |

Primary Examiner—Robert J. Warden
Assistant Examiner—Laura E. Collins
Attorney, Agent, or Firm—Rosenbaum & Schwartz

[57] ABSTRACT

An incense burner consisting of an upright cylindrical tube supported on a base and having a vent opening located in relatively closer proximity to the base than to an upper opening of the tube. A spring clip is provided to hold an incense stick in an inverted position within the cylindrical tube and above the vent opening to facilitate combustion of the incense.

12 Claims, 1 Drawing Sheet

INCENSE BURNER

BACKGROUND OF THE INVENTION

The present invention relates generally to devices for holding a stick of combustible incense and containing ash resulting from the combustion of the incense. More specifically, the present invention relates to an upright cylindrical tube member having a means for retaining the incense in a supported condition within the tube and a vent aperture to permit intake of air to support combustion of the incense.

A number of incense burners of varying configuration have been patented or have been manufactured. Perhaps the most common incense burner is configured as an elongate tray having a relative upright portion which has a bore to retain an incense stick in a suspended position above the tray. This configuration permits combustion of the incense to occur above the tray and ash resulting from the combustion to fall into the tray. Other types of incense burners are also known. U.S. Pat. No. 4,275,748 discloses an elongated rectangular box having a removable bottom wall carrying an intermediate vertical wall running the length of the box. The intermediate wall divides the box into two compartments for storing a supply of stick incense. An incense burner is removably mounted onto the top of the box. U.S. Pat. No. 4,237,097 discloses an incense burner consisting of a hollow housing having a pyramid shape and a vent aperture in one of the side walls adjacent to the apex. U.S. Pat. No. 4,198,375 also discloses an incense burner consisting of an exterior receptacle fitted with an ash collecting basket which also supports a lighter within the receptacle. A disk is supported on an axially-disposed spindle within the receptacle and retains incense sticks within a plurality of folds in the disk. U.S. Pat. No. 4,178,346 discloses an incense burner device adaptable for use in an automotive vehicle. This device consists of an open-ended container having a stem, the stem having a clamp which is attachable to the edge of an ashtray within an automobile. U.S. Pat. No. 4,155,979 discloses an incense burner and storage device consisting of an upright back plate formed with a pocket for holding sticks of incense and a means associated with the back plate to suspend the plate from a door. The device further has an elongated base member formed with a longitudinal channel and a recess to removably support a chimney having a cap to permit smoke to escape through the cap. U.S. Pat. No. 3,605,437 discloses an article of jewelry including an incense burner which is an open casing or ring supporting an open mesh basket in which a pellet of incense can be set and ignited. Other examples of various incense burners or holders are found in U.S. Pat. Nos. 4,700,721, 4,347,217 and U.S. Design Patent Nos. D264,869 and D255,708.

None of the foregoing patents disclose a simple, easy to use, easy to manufacture incense burner which consists principally of an upright tubular enclosure having a base member attached to and enclosing one end of the tubular member and the tubular member being open at a top end thereof. A vent opening is laterally provided in the wall of the tubular member and is located above, but in relatively closer proximity to the lower end of the tubular enclosure than to the upper end of the tubular enclosure. In conjunction with the tubular enclosure, there should be provided a clip to engage a piece of combustible incense, preferably an incense bearing stick in an inverted position and substantially centrally positioned in the tubular enclosure. The vent opening should be positioned below the lowest point on the incense bearing stick to facilitate drawing of air into the tubular enclosure to facilitate combustion.

SUMMARY OF THE INVENTION

It is a broad object of the invention to provide a stable, compact, upstanding enclosure for holding and burning an incense bearing a piece of incense. The incense burner consists of an upstanding tubular member having a vent opening and a clip to hold the combustible incense in an inverted position within the lumen of the tubular enclosure. The tubular enclosure will be supported on a base, and the base may be weighted depending upon the height of the tubular enclosure.

DETAILED DESCRIPTION OF THE PREFERRED EMBODIMENT

Figure 1:
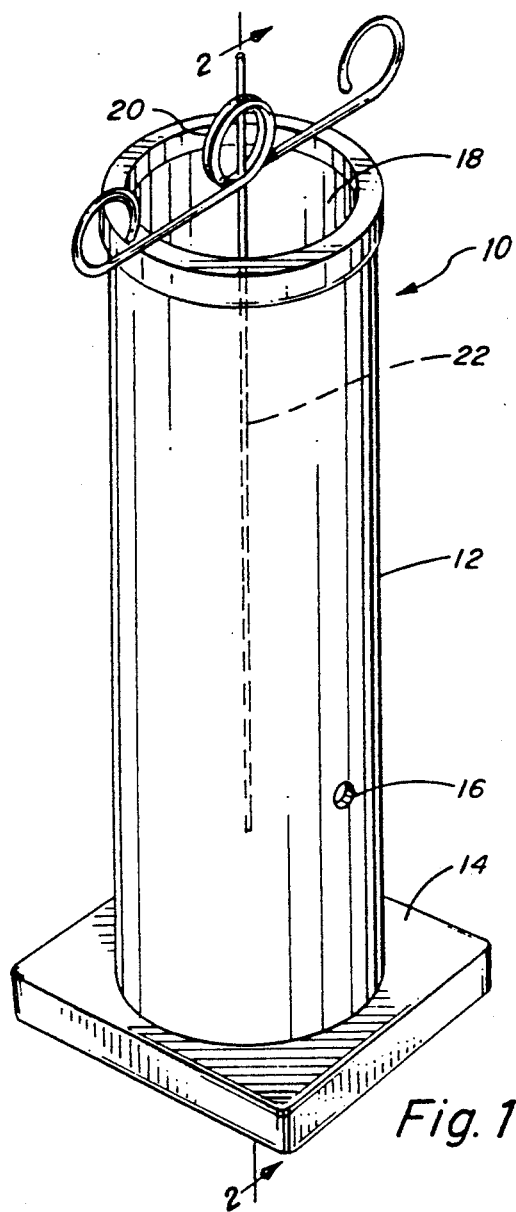
FIG. 1 is a perspective view of the incense burner apparatus of the present invention.
Figure 2:
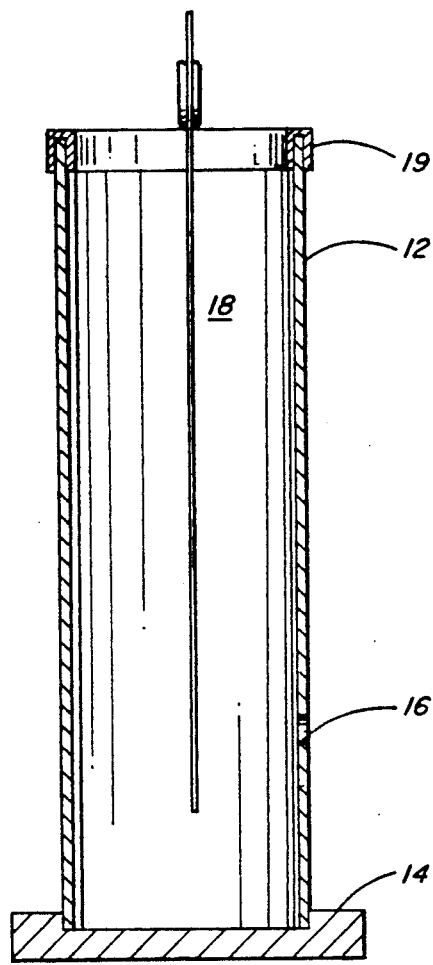
FIG. 2 is a cross-sectional view taken along line 2—2 of FIG. 1.
Figure 3:
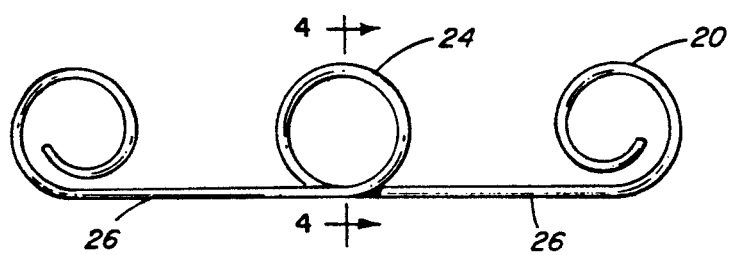
FIG. 3 is a side elevational view of a spring clip member for use with the incense burner of the present invention.
Figure 4:
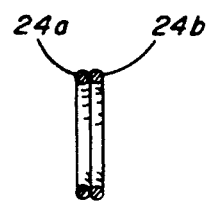
FIG. 4 is a cross-sectional view taken along line 4—4 of FIG. 3.

Turning now to the accompanying FIGS. 1–4, there is illustrated the preferred embodiment of the incense burner in accordance with the present invention. The incense burner 10 of the invention consists generally of a tubular member 12 which is coupled to a base 14 in an upright position. The connection between base 14 and tubular member 12 seals a first end of the tubular member in a closed engagement. A second end of the tubular member remains open. It is desirable, according to the preferred embodiment, to provide an annular cap 19 engaged upon a peripheral edge of tubular member 12 to form a protective cap therefor. A vent opening 16 is provided in the wall of the tubular member 12 and is preferably located in relatively closer proximity to the first closed end of the tubular member 12 adjacent the base 14, than to the second open end of the tubular member 12. In accordance with the best mode of the invention, the vent opening will have a diameter in the range of approximately $\frac{1}{8}''$ to $\frac{3}{8}''$, and is preferably $\frac{1}{4}''$ diameter. The vent opening 16 will also preferably be located approximately 3" to 4" above the base 14, and preferably is approximately 3 ½ from the base 14. The length of the tubular member 12 may be any length desired by the manufacturer or user, but preferably will correspond to the lengths of commercially available incense, i.e., 9" to 10" sticks up to about 30" sticks. In conjunction with the tubular member illustrated in FIGS. 1 and 2, there is also provided a clip member 20 for engaging onto an incense stick 22 and being supported by a peripheral edge of the open end of the tubular member 12. The clip 20 is preferably a spring clip having a double looped configuration as illustrated in FIGS. 3 and 4. The incense stick is placed within a central double loop of the clip member 20 and retained in an inverted position within a lumen 18 of the tubular member 12. The clip member 20 preferably consists of a single piece of spring metal, which is configured as a central double loop spring 24, consisting of two spring loops 24a and 24b, each of which has ends which project laterally as legs 26. Legs 26 may be deflected or deformed to actuate opening of a space between double loop rings 24a and 24b of sufficient size to engage the incense stick 22.

Those skilled in the art will appreciate that the present invention provides an incense burner which will facilitate an adequate air flow to support combustion within the lumen 18 of the tubular member 12. The combusting incense will result in an ash residue which can fall into the lower part of the tubular member 12 below vent opening 16. Thus, the incense burner 10 of the invention will provide a relatively compact, easy to use and easy to manufacture unit for retaining and burning a piece of incense and for retaining the resulting ash which is the product of incense combustion. The tubular member is preferably made of a plastic material, such as a clear, translucent, colored, or opaque polycarbonate material, or may be made of a lightweight metal, such as aluminum or titanium, such as will be suitable for containing and retaining combustible materials, heat and ash. The base 14 may also be made of a plastic material or a metal material, and may be either weighted or unweighted depending upon the height of the tubular member 12.

Thus, there has been described an incense burner and incense holder in accordance with the best mode of the invention and illustrated with reference to the preferred embodiments thereof. Those skilled in the art will understand and appreciate from the foregoing that variations in size, selection of materials and methods for constructing the basic device may be varied and still remain within the spirit and scope of the invention, which is intended only to be limited by the claims appended hereto.

I claim:
1. An incense burner, comprising:
   an upstanding tubular member defining an interior lumen and having a first end, a second end, and a midpoint between said first and second ends;
   a base member attached to said first end of said tubular member and enclosing said first end of said tubular member;
   a vent aperture disposed in a wall of said tubular member between said midpoint and said first end of said tubular member; and
   clip means for retaining an incense stick in an inverted position within said lumen of said tubular member comprising a double loop spring comprising two adjacent loops, each of said two adjacent loops comprising a leg portion continuously extending from each of said two adjacent loops, whereby compression of each leg portion causes enlargement of each of said two adjacent loops, whereby an opening between each of said two adjacent loops is formed, said opening being of sufficient size to engage an incense stick.
2. The incense burner of claim 1, wherein said base member is weighted.
3. The incense burner of claim 1 wherein said tubular member further comprises an upper ring adapted to engage an upper peripheral edge of said second end of said tubular member.
4. The incense burner of claim 1, wherein said tubular member further comprises at least one of a plastic material of a metal material.
5. The incense burner of claim 1, wherein said vent aperture is about 150 " to about ⅛" in diameter.
6. The incense burner of claim 5, wherein said vent aperture is positioned about 3" to about 4" from said member.
7. An incense burner, comprising in combination:
   an upright tubular member having an open interior lumen, a first end, a second end, and a midpoint between said first and second ends;
   a base member coupled to said first end of said tubular member and enclosing said first end of said tubular member, said base member supporting said upright tubular member in an upstanding position;
   a vent opening in a side wall of said tubular member, said vent opening being between said midpoint and said first end of said tubular member; and
   a spring clip member removably mounted upon said second end of said tubular member comprising a double loop spring comprising two adjacent loops, each of said two adjacent loops comprising a leg portion continuously extending from each of said two adjacent loops, whereby compression of each leg portion causes enlargement of each of said two adjacent loops, whereby an opening between each of said two adjacent loops is formed, said opening being of sufficient size to engage an incense stick.
8. The incense burner of claim 7, wherein said base member is weighted.
9. The incense burner of claim 7, wherein said tubular member further comprises an upper ring adapted to engage an upper peripheral edge of said second end of said tubular member.
10. The incense burner of claim 7, wherein said tubular member further comprises at least one of a plastic material or metal material.
11. The incense burner of claim 7, wherein said vent aperture is about ⅛" to about ½" in diameter.
12. The incense burner of claim 11, wherein said vent aperture is positioned about 3" to about 4" from said base member.

* * * * *